United States Patent
Harshman et al.

(10) Patent No.: US 11,986,167 B2
(45) Date of Patent: May 21, 2024

(54) SYSTEMS AND METHODS FOR REAL-TIME SWEAT SAMPLING AND ANALYSIS

(71) Applicant: Government of the United States, as represented by the Secretary of the Air Force, Wright-Patterson AFB, OH (US)

(72) Inventors: Sean Harshman, Fairborn, OH (US); Anthony Qualley, Washington Township, OH (US); Amanda Bowman, Miamisburg, OH (US); Kraig Strayer, Fairborn, OH (US); Rhonda Pitsch, Springfield, OH (US); Michael Brothers, Lebanon, OH (US)

(73) Assignee: The Government of the United States of America as Represented by the Secretary of the Air Force, Wright-Patterson AFB, OH (US)

(*) Notice: Subject to any disclaimer, the term of this patent is extended or adjusted under 35 U.S.C. 154(b) by 0 days.

(21) Appl. No.: 18/194,630

(22) Filed: Apr. 1, 2023

(65) Prior Publication Data

US 2023/0240668 A1  Aug. 3, 2023

Related U.S. Application Data

(62) Division of application No. 17/329,252, filed on May 25, 2021, now Pat. No. 11,707,262.

(Continued)

(51) Int. Cl.
*A61B 10/00* (2006.01)
*A61B 5/00* (2006.01)

(52) U.S. Cl.
CPC ........ *A61B 10/0064* (2013.01); *A61B 5/4266* (2013.01); *A61B 5/443* (2013.01); *A61B 5/6824* (2013.01); *A61B 5/6831* (2013.01)

(58) Field of Classification Search
CPC ... A61B 10/0064; A61B 5/4266; A61B 5/443; A61B 5/6824; A61B 5/6831
See application file for complete search history.

(56) References Cited

U.S. PATENT DOCUMENTS

| | | |
|---|---|---|
| 3,635,213 A | 1/1972 | LaHay |
| 4,190,060 A | 2/1980 | Greenleaf et al. |

(Continued)

OTHER PUBLICATIONS

Pandolf, et al., Physiological Strain During Light Exercise in Hot-Humid Environments, Aerospace Medicine, Apr. 1974, pp. 359-365, vol. 45, No. 4, publisher unknown.

(Continued)

*Primary Examiner* — Eric F Winakur
*Assistant Examiner* — Abid A Mustansir
(74) *Attorney, Agent, or Firm* — AFMCLO/JAZ; Jeffrey V. Bamber (57) ABSTRACT

Systems and methods for continuous real-time sweat sampling and analysis are disclosed. A sweat collection article and method of collecting sweat from a person's skin using the sweat collection article are provided. The sweat collection article includes: a sweat collecting tube placed adjacent to the person's skin, and at least one piece of flexible material that has an adhesive that adheres the article to the person's skin and is positioned to overlie one end of the tube. The second end of the sweat collecting tube is in fluid communication with an instrument such as a mass spectrometer that analyzes the sweat on a real-time basis. The systems and methods may further include a device for removing salt from the sweat that is arranged so that the sweat is transported to the device prior to being transported to the instrument for analyzing the sweat.

7 Claims, 3 Drawing Sheets

Related U.S. Application Data (60) Provisional application No. 63/083,403, filed on Sep. 25, 2020.

(56) References Cited

U.S. PATENT DOCUMENTS

| | | | |
|---|---|---|---|
| 4,383,529 A | | 5/1983 | Webster |
| 4,398,543 A | | 8/1983 | Sandlin et al. |
| 4,542,751 A | | 9/1985 | Webster et al. |
| 5,282,939 A | * | 2/1994 | Voss .................... C09B 67/0096 204/529 |
| 6,198,953 B1 | | 3/2001 | Webster et al. |
| 9,226,730 B2 | | 1/2016 | Briscoe et al. |
| 10,548,574 B2 | | 2/2020 | Briscoe et al. |
| 10,674,946 B2 | | 6/2020 | Begtrup et al. |
| 2011/0275918 A1 | * | 11/2011 | Yamashita ........... A61B 5/1495 604/93.01 |
| 2013/0183399 A1 | | 7/2013 | Blow et al. |
| 2014/0276220 A1 | * | 9/2014 | Briscoe ................ A61B 5/4266 600/580 |
| 2015/0057515 A1 | | 2/2015 | Hagen et al. |
| 2016/0262667 A1 | | 9/2016 | Pizer et al. |
| 2016/0374598 A1 | | 12/2016 | Heikenfeld et al. |
| 2019/0209062 A1 | | 7/2019 | Choi et al. |
| 2019/0290248 A1 | | 9/2019 | Katchman et al. |
| 2019/0365298 A1 | | 12/2019 | Harshman et al. |
| 2021/0223168 A1 | * | 7/2021 | Messerschmidt ...... A61B 5/157 |
| 2022/0096058 A1 | | 3/2022 | Harshman et al. |

OTHER PUBLICATIONS

Liappis, et al., Quantitative Study of Free Amino Acids in Human Eccrine Sweat Excreted from the Forearms of Healthy Trained and Untrained Men During Exercise, European Journal of Applied Physiology, Oct. 1979, pp. 227-234, vol. 42, Springer-Verlag.

Boysen, et al., A Modified Anaerobic Method of Sweat Collection, J. Applied Physiology: Resiprat. Environ. Exercise Physiology, 1984, pp. 1302-1307, the American Physiology Society, Rockville, MD.

Shiffeffs, et al., Whole Body Sweat Collection in Humans: An Improved Method With Preliminary Data on Electrolyte Content, 1997, pp. 336-341, the American Physiology Society, Rockville, MD.

Patterson, et al., Effect of Induced Metabolic Alkolosis on Sweat Composition in Men, Acta Physiol Scand, 2002, pp. 41-46, vol. 174, Scandinavian Physiological Society.

Hayden, et al., The Reproducibility of Closed-Pouch Sweat Collection and Thermoregulatory Responses to Exercise-Heat Stress, European Journal of Applied Physiology, Feb. 2004, pp. 748-751, vol. 91, Springer-Verlag.

Morgan, et al., Acute Effects of Dehydration on Sweat Composition in Men During Prolonged Exercise in the Heat, Acta Physiol Scand, 2004, pp. 37-43, vol. 182, Scandinavian Physiological Society.

Saat, et al., Effects of Short-Term Exercise in the Heat on Thermoregulation, Blood Parameters, Sweat Secretion and Sweat Composition of Tropic-Dwelling Subjects, Journal of Physiological Anthropology and Applied Human Science, 2005, pp. 541-549, vol. 24, published at http://www.jstage.jst.go.jp/browse/jpa.

Meyer, et al., Effect of Age and Gender on Sweat Lactate and Ammonia Concentrations During Exercise in the Heat, Brazilian Journal of Medical and Biological Research, 2007, pp. 135-143, vol. 40, Associacao Brasileira de Divulgacao Cientifica.

Kutyshenko, et al., Analyzing and Mapping Sweat Metabolomics by High-Resolution NMR Spectroscopy, PLoS One vol. 6 (Issue 12), https://doi.org/10.1371/journal.pone.0028824.

Mark, et al., Amino Acid Composition, Including Key Derivatives of Eccrine Sweat: Potential Biomarkers of Certain Atopic Skin Conditions, International Journal of Cosmetic Science, 2013, vol. 35, pp. 163-168, Society of Cosmetic Scientists and the Societe Francaise de Cosmetologic.

Calderon-Santiago, et al., Optimization Study for Metabolomics Analysis of Human Sweat by Liquid Chromatography-Tandem Mass Spectrometry in High Resolution, Journal of Chromatography A, 1333, 2014, pp. 70-78, Elsevier B.V.

Calderon-Santiago, et al., Human Sweat Metabolomics for Lung Cancer Screening, Anal Bioanal Chem, 2015, vol. 407, pp. 5381-5392, Springer-Verlag Berlin, Heidelberg, Germany.

Csosz, et al., Highly Abundant Defense Proteins in Human Sweat as Revealed by Targeted Proteomics and Label Free Quantification Mass Spectrometry, J Eur Acad Dermatol Venereol, Oct. 2015, vol. 29 (10), pp. 2024-2031.

Clarys, et. al., Estimation of Sweat Rates During Cycling Exercise by Means of the Closed Chamber Condenser Technology, Skin Research and Technology, 2017, vol. 23, pp. 30-35, published by John Wiley & Sons Ltd.

Delgado-Povedano, et al., Recent Advances in Human Sweat Metabolomics for Lung Cancer Screening, Metabolomics 2016, p. 166, vol. 12, Springer Science + Business Media, New York.

Dunstan, et al., Sweat Facilitated Amino Acid Losses in Male Athletes During Exercise at 32-34oC, published Dec. 9, 2016, PLoS One, vol. 11 (Issue 12), https://doi.org/10.1371/journal.pone.0167844.

Yu, et al., Proteomic and Peptidomic Analysis of Human Sweat With Emphasis on Proteolysis, Journal of Proteomics, vol. 155, 2017, pp. 40-48, Elsevier B.V.

Delgado-Povedano, et al., Metabolomics Analysis of Human Sweat Collected After Moderate Exercise, Talanta 177, 2018, pp. 47-65, Elsevier B.V.

Harshman, et al., The Proteomonic and Metabolomic Characterization of Exercise-Induced Sweat for Human Performance Monitoring: A Pilot Investigation, published Nov. 1, 2018, PLoS One vol. 13 (Issue 11), https://doi.org/10.1371/journal.pone.0203133.

Harshman, et al., Metabolomic Stability of Exercise-Induced Sweat, Journal of Chromatography B, 1126-1127, 2019, Elsevier B.V.

* cited by examiner

SYSTEMS AND METHODS FOR REAL-TIME SWEAT SAMPLING AND ANALYSIS

This application is a division of application Ser. No. 17/329,252 filed May 25, 2021, which claims the benefit of and priority to Provisional Application Ser. No. 63/083,403, filed Sep. 25, 2020, which is expressly incorporated herein by reference.

RIGHTS OF THE GOVERNMENT

The invention described herein may be manufactured and used by or for the Government of the United States for all governmental purposes without the payment of any royalty.

FIELD OF THE INVENTION

The present invention relates generally to the collection of human sweat for analytical evaluation and, more particularly, to systems and methods for real-time sweat sampling and analysis.

BACKGROUND OF THE INVENTION

Sweat has become an emerging biosource for biomarker discovery to sustain or enhance human performance. Typically, single large bulk sweat samples are collected for later off-line analysis. While useful, this sampling strategy limits the time-resolution of often-lengthy collection events and the utility of identified markers.

Historically, the most widely used method for sweat collections involves a single sample, obtained via a "patch" or other device, collected over the course of an entire experiment, such as an exercise or sweat stimulation regime. Therefore, the sample collected is only representative of the mean analyte concentration over the experimental time. As a result, changes of analytes, e.g. ions and metabolites, over the time course of the experiment are lost.

Therefore, a need exists for a system and method for real-time sweat sampling and analysis to better elucidate any changes in properties of the sweat and/or analyte concentration that may occur during the course of an experiment.

SUMMARY OF THE INVENTION

While the invention will be described in connection with certain embodiments, it will be understood that the invention is not limited to these embodiments. To the contrary, this invention includes all alternatives, modifications, and equivalents as may be included within the spirit and scope of the present invention.

The present invention relates generally to the collection of human sweat for analytical evaluation and, more particularly, to systems and methods for continuous real-time sweat sampling and analysis. Several embodiments of the sweat collection and analysis system are described herein.

The first embodiment provides a continuous real-time sweat collection system comprising a sweat collecting device comprising a main body having two surfaces comprising a sweat-collecting surface and an opposing outwardly-oriented surface. The sweat-collecting surface has a concave configuration which defines a rim lying wholly within a common plane. The main body has an axial bore extending between the sweat-collecting surface and the outwardly-oriented surface. A length of sweat collector tubing has one end joined to the main body at the axial bore and a free end that extends outwardly from the outwardly-oriented surface of the main body. The free end of the sweat collector tubing is in fluid communication with the input or source of a detector or instrument such as a mass spectrometer.

The method of using the first embodiment of the sweat collection system comprises:
a) placing a sweat collection device over an area of the person's skin, wherein the sweat collection device comprises:
   a main body having two surfaces comprising a sweat-collecting surface and an opposing outwardly-oriented surface, wherein the sweat-collecting surface has a concave configuration which defines a rim lying wholly within a common plane, wherein the main body has an axial bore extending between the sweat-collecting surface and the outwardly-oriented surface; and
   a length of sweat collector tubing having one end joined to the main body at the axial bore and a free end extending outwardly from the outwardly-oriented surface of the main body;
b) placing the free end of the sweat collector tubing in fluid communication with the input port of an instrument for analyzing sweat;
c) collecting sweat from the person's skin using the sweat collection device wherein sweat travels into the sweat collector tubing and then into the instrument; and
d) analyzing the sweat collected using the instrument.

The second embodiment provides a continuous real-time sweat collection system which comprises a sweat collecting article and a sweat collector tube. The sweat collecting article comprises a thin, flexible, conformable, and impervious covering. The covering has two surfaces comprising a body-facing surface and an opposing outwardly-oriented surface. The covering comprises a central portion, edges that define a perimeter, and a perimeter portion surrounding the central portion. The central portion of the body-facing surface is free of adhesive. The perimeter portion has adhesive on the body-facing surface for adhering the covering to a person's skin and for forming a seal around the central portion.

In the second embodiment, the sweat collector tube has a first end, a second end, and a length that extends between the first and second ends. The first end of the sweat collector tube is positioned adjacent to the covering so that the central portion of the covering overlaps a first portion of the tube. A second portion of the tube extends outward beyond one edge of the central portion of the covering and is adjacent to and is joined to the adhesive on the perimeter portion of the covering. A third portion of the tube extends beyond an edge of the covering to the second end of the tube. The second end of the tube is free to be placed in fluid communication with an instrument for analyzing the sweat.

The method of using the second embodiment of the sweat collection system comprises:
a) attaching a sweat collection article over an area of the person's skin, wherein the sweat collection article comprises:
   a sweat collector tube having a first end and a second end, wherein the first end of the tube is placed adjacent the area of the person's skin, and the second end of sweat collector tube is free to be placed in fluid communication with an instrument for analyzing sweat; and
   a thin, flexible, conformable, and impervious covering that is positioned over and adhered to the sweat collector tube, the covering having two surfaces comprising a body-facing surface and an opposing outwardly-oriented surface, a central portion, edges that define a perimeter of said central portion, and a perimeter portion surrounding the central portion, wherein the central portion of the body-facing surface is free of adhesive, and the central portion of the covering is placed over the first end of the sweat collector tube, and the perimeter portion has adhesive on the body-facing surface for adhering the covering to a person's skin and for forming a seal around the central portion;

b) placing the free second end of the sweat collector tube in fluid communication with the input port of an instrument for analyzing sweat;

c) collecting sweat from the person's skin using the sweat collection device wherein sweat travels into the sweat collector tubing and then into the instrument; and d) analyzing the sweat collected using the instrument.

In addition, in any of the embodiments described above, or in other embodiments, salt may be removed from the sweat before it is transported to an instrument for analyzing sweat. An example of such an embodiment is a continuous real-time sweat collection and analysis system comprising:

a sweat collecting device comprising:
an article that is to be placed in contact with an area of a person's skin, the article having a skin-facing surface, wherein the article is configured to collect sweat between the area of skin and the skin-facing surface; and a sweat collector tube having one end that is positioned adjacent to the article and in position to withdraw and transport sweat collected between the area of skin and the skin-facing surface of the article, the tube extending outwardly from the article to a free end;

a device for removing salt from the sweat, the device having an input port and an output port, wherein the free end of the sweat collector tubing is in fluid communication with the input port of the device for removing salt from the sweat; and an instrument for analyzing sweat having an input port, wherein the input port of the instrument is in fluid communication with the output port of the device for removing salt from the sweat.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

The present invention relates generally to the collection of human sweat for analytical evaluation and, more particularly, to systems and methods for continuous real-time sweat sampling and analysis.

Figure 1:
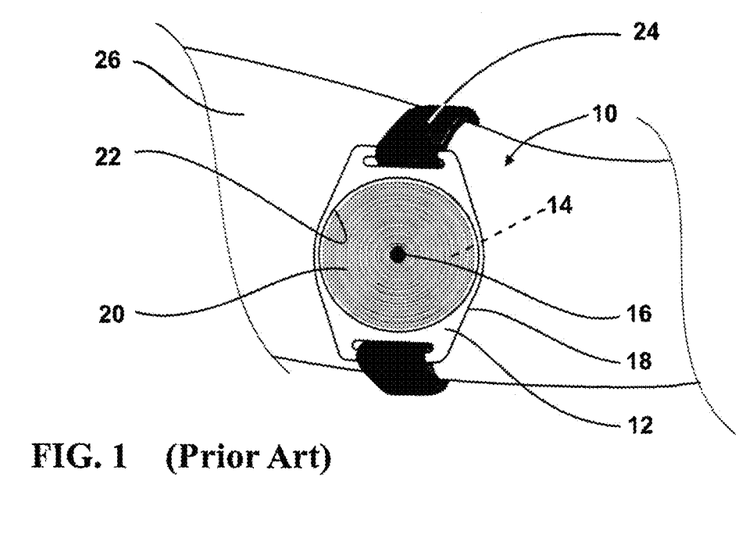
FIG. 1 is a perspective view of a prior art sweat collection device attached to a portion of a wearer's forearm.

FIG. 1 shows a prior art sweat collection device 10 attached to a portion of a person's forearm. The prior art sweat collection device 10 shown is a MEGADUCT® sweat testing device sold by ELITechGroup of Logan, Utah, U.S.A. ELITechGroup also sells a similar, but smaller MACRODUCT® sweat collection device. These products and the procedure for using the same are described in greater detail in U.S. Pat. No. 4,383,529, Webster and U.S. Pat. No. 4,542,751, Webster, et al. The sweat collection device 10 is typically used in a process to determine the concentration of sodium and chloride in the sweat of children suffering from cystic fibrosis. U.S. Pat. No. 4,383,529, Webster discloses an iontophoretic electrode device that is used with an iontophoretic drug such as pilocarpine to induce sweating at a selected area of a person's skin prior to placing the sweat collection device against the person's skin. Certain improvements to these products are described in U.S. Pat. No. 6,198,953 B1, Webster, et al. and U.S. Pat. No. 9,226,730 B2, Briscoe, et al.

The MEGADUCT® sweat collection device 10, as described in the aforementioned patents, comprises a solid body 12 having a concave means defined at a face thereof by a sweat-collecting surface 14 which gradually recedes from a rim lying wholly within a common plane. In FIG. 1, the sweat-collecting surface 14 is facing the wearer's skin. An axial bore 16 extends from the sweat-collecting surface to the opposite face 18 of the solid body. The maximum depth of the concave means is such that the skin and flesh of the flat area of a human body to which the device is applied will bulge into contact with the sweat-collecting surface 14 over substantially the entire area thereof when the rim is placed firmly against the skin of the flat area of the human body, leaving substantially no dead space in the interface between the bulged skin and the sweat-collecting surface 14. The body secretion pressure of sweat will force sweat through the interface to the axial bore 16. The axial bore 16 is adapted to connect with a length of flexible, sweat collector tubing 20 at the opposite face 18 of the solid body 12. The sweat collector tubing 20 is coiled in a flat, spiral formation and is positioned within a recessed receiving chamber 22 on the face 18 of the body 12 opposite the sweat-collecting surface 14. The solid body 12 is fastened against the flat area of a portion 26 of a human body such as by straps 24 so as to maintain firm placement of the rim and sweat-collecting surface 14 against the skin.

U.S. Pat. No. 4,542,751, Webster, et al. describes how the sample of sweat is obtained when using the MEGADUCT® sweat collection device after it is collected in the spiral tubing. The tubing 20 has to be disconnected from the axial bore 16. The sweat then has to be expelled from the tubing 20 into a testing vessel by inserting an elastomer bulb into one end of the tubing 20 and squeezing the bulb. As a result, all of the sweat collected in the tubing is mixed together in the testing vessel. Because of this, it is not possible to analyze samples of sweat obtained at different times during the collection period.

Figure 2:
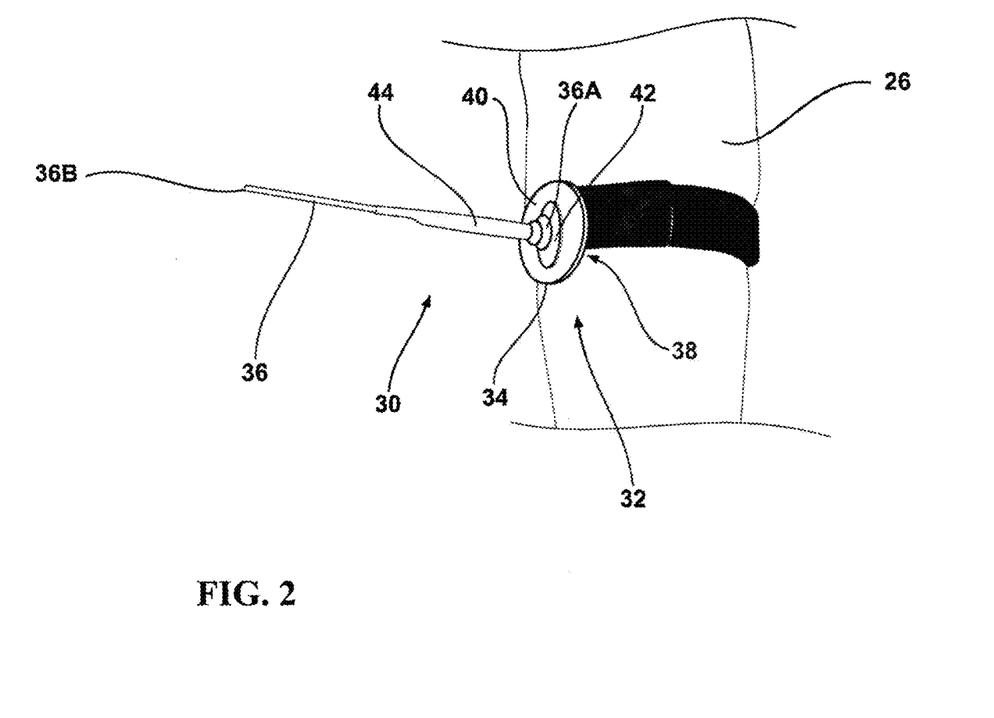
FIG. 2 is a perspective view of a first embodiment of sweat collection device shown on a person's arm oriented downward as it might be if the person is on a treadmill.

FIG. 2 shows a first embodiment of the sweat collecting device used in the sweat collection and analysis system and method of the present invention. This sweat collecting device and sweat collection and analysis system and method constitutes an improvement over the MACRODUCT® and MEGADUCT® sweat collection devices and current procedures for using the same in order to provide continuous real-time sweat sampling and analysis.

The term "continuous", as used herein, refers to sampling and analysis that takes place on an uninterrupted basis from the time the analytical instrument is started and sweat is received by the instrument. It is also within the scope of the present invention, however, for the sweat collection and analysis systems and methods to be operated in a non-continuous manner by interrupting the sampling and analysis, if desired.

The term "real-time", as used herein, refers to a process in which the analysis is taking place as the sweat is being collected, rather than a process that involves collecting and storing the sweat for later analysis. The analysis will occur without placing the sweat in a separate container prior to conducting the analysis. Instead, the sweat may be transported by a conduit or tube directly to an analytical instrument (or after it has been processed by removing salt from the same as described herein). The time period in which the analysis may occur may be less than or equal to any of the following time periods after the generation of the sweat being analyzed: 15, 10, 5, 3, 2, or 1 minutes.

The terms "tube" and "tubing" may be used interchangeably herein. The tubing referred to herein is typically flexible along its entire length, although it is possible for portions of the tubing that do not move or conform to the body of the test subject during use to be relatively rigid.

Figure 6:
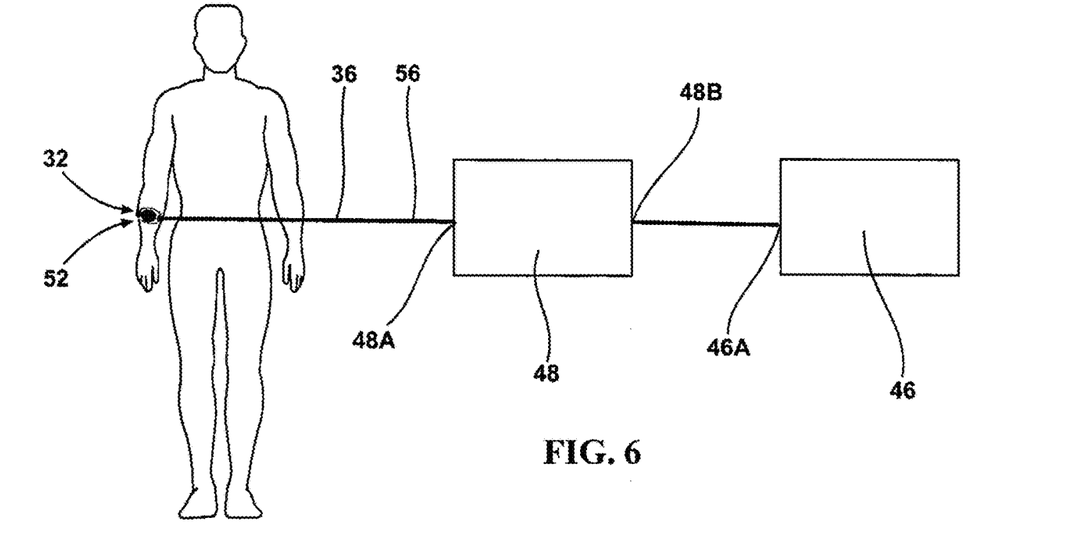
FIG. 6 is a schematic side view of a sweat collection and analysis system comprising a device for removing salt from the sweat before it is transported to an instrument for analysis.

The first embodiment of the sweat collection system 30 comprises a sweat collecting device 32 comprising a main body 34 and a length of sweat collector tubing 36. The main body 34 has two surfaces comprising a sweat-collecting surface 38 and an opposing outwardly-oriented surface 40. The sweat-collecting surface 38 has a concave configuration which defines a rim lying wholly within a common plane. The main body 34 has an axial bore 42 extending between the sweat-collecting surface 38 and the outwardly-oriented surface 40. The axial bore 42 is covered by other components in FIG. 2, but it is in the location of the end of the lead line pointing to the same. The sweat collecting tubing 36 has a first end 36A joined to the main body 34 at the axial bore 42, and extends outwardly from the outwardly-oriented surface 40 of the main body 34 of the sweat collecting device 32 to a free second end 36B that is in fluid communication with an instrument for analyzing sweat (such an instrument is shown in FIG. 6).

The sweat collector tubing (or "tube") 36 should have a length and an inside diameter that permits the transport of sweat therethrough at a rate which is sufficient to provide the sweat to an instrument for analyzing the sweat on a continuous real-time basis, or approximately real-time basis. It may be desirable for the person from whom sweat is being collected to be positioned close to the instrument to ensure that there is minimal delay between the sweat collection and the analysis. In some cases, it may, for example, be desirable for the participant to be within about 0.5 meter of the instrument. The length of the tubing 36 may, therefore, be less than or equal to about 0.5, 0.6, or 0.7 meter, or more. The inside diameter of the tubing 36 can be any size that is a small enough to transport sweat under the body secretion pressure yet large enough to transport a sufficient amount of the sweat to the instrument for analysis on a real-time basis. The inside diameter of the tubing should also be sufficiently small that there is substantially no mixing of the sweat obtained at various times during the sweat collection process. The inside diameter of the tubing 36 may be less than 0.85 mm, or less than (or less than or equal to about) 0.8 mm or 0.75 mm. In one embodiment, the tubing 36 has an inside diameter of about 0.01 inch (about 0.25 mm). Thus, the inside diameter of the tubing 36 may range from about 0.01 inch (about 0.25 mm) or less (e.g., about 0.2 mm) up to 0.85 mm. The sweat collector tube 36 can comprise any suitable material including, but not limited to polyetheretherketone (PEEK) tubing.

The main body 34 of the device can have a support 44 joined thereto such as to the outwardly-oriented surface 40 of the same for supporting the sweat collector tubing 36 during the sweat collection activity. The support 44 can comprise any suitable member or structure. The support 44 shown in FIG. 2 comprises a plastic dowel that is placed adjacent to the tubing so that it runs along the length of a section of the tubing that extends from the outwardly-oriented surface 40 of the main body 34 of the device, and the dowel and section of tubing are held together with a heat shrink wrap.

The first embodiment of the sweat collection device 32 can be made by modifying a MEGADUCT® sweat collecting device by removing the sweat collector tubing that is provided. The main body 34 of the sweat collection device 32 may, thus, have any of the properties of the solid body of the MEGADUCT® device described above. The sweat collector tubing 20 that is supplied with the MEGADUCT® device has an inside diameter of about 0.86 mm (about 0.34 inches) according to the patents referenced above. While this is suitable for collecting and storing sweat, it is not suitable for transporting sweat therethrough at a rate which is sufficient to provide the sweat to an instrument for analyzing the sweat on a real-time basis. It is estimated that the MEGADUCT® tubing may require as much as one hour to transport a sufficient quantity of sweat for analysis. The sweat collector tubing can be replaced with the PEEK tubing described above.

The free second end 36B of the sweat collector tubing 36 is placed in fluid communication (directly, or indirectly) with the input (or source) 46A of a detector or instrument for analyzing sweat 46 as shown in FIG. 6. The instrument for analyzing sweat 46 may be any suitable type of instrument that provides information about the composition of the sweat, particularly on a continuous, real time basis. Suitable instruments include, but are not limited to mass spectrometers, UV spectrophotometers, ion chromatography devices, proton-transfer-reaction mass spectrometers (PTR-MS). Any suitable type of mass spectrometer that allows the sweat to be analyzed on a continuous, real time basis can be used. Suitable types include electrospray ionization (ESI) mass spectrometers. One suitable ESI mass spectrometer is a FUSION LUMOS™ available from Thermo Fisher Scientific of Waltham, MA, U.S.A.

Figure 3:
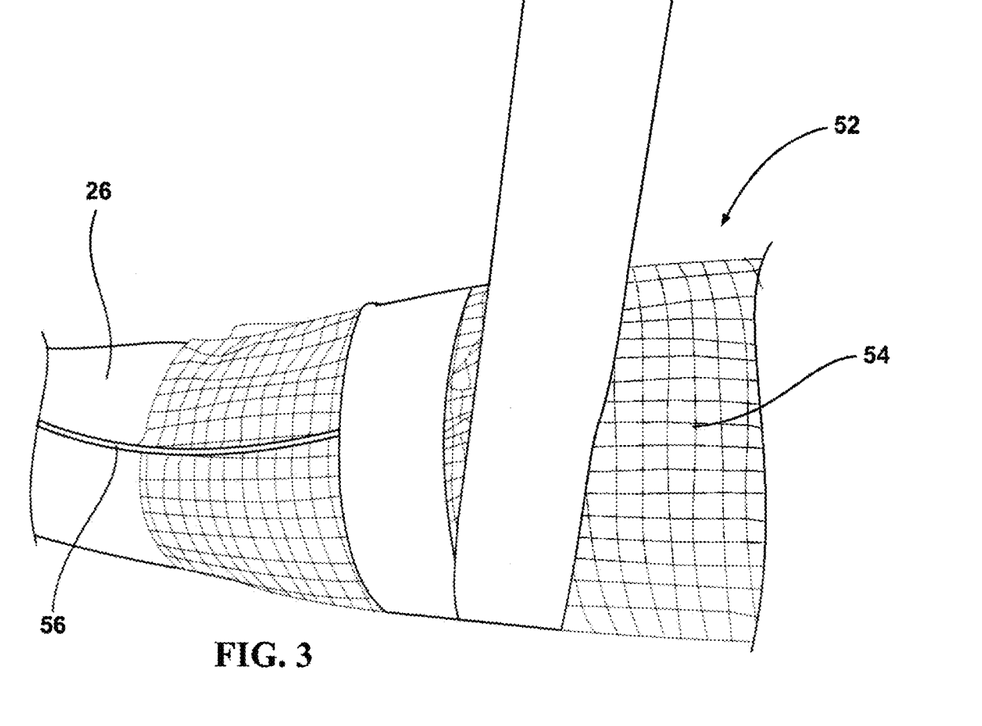
FIG. 3 is a perspective view of a second embodiment of the sweat collection device described herein attached to a portion of a wearer's forearm.

FIG. 3 shows a second embodiment of a sweat collection device comprising a sweat collecting article 52 that is used in the sweat collection and analysis system and method of the present invention. The second embodiment of a sweat collection device is shown attached to a portion 26 of a wearer's forearm. The sweat collecting article 52 comprises a covering 54 and a sweat collector tube 56. Two versions of the second embodiment of the sweat collecting article 52 are shown in the drawings.

Figure 4:
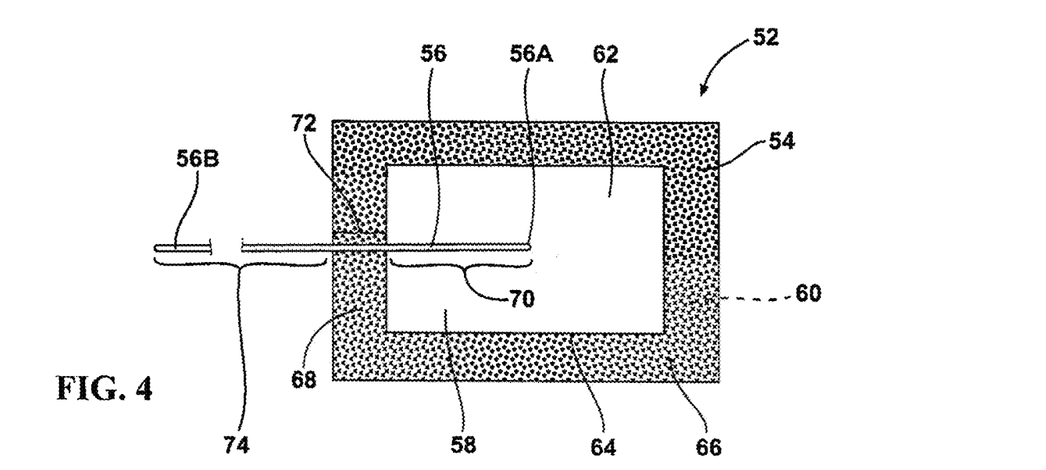
FIG. 4 is a bottom plan view of one version of the second embodiment of the sweat collection device.

FIG. 4 shows a first version of the sweat collecting article 52 of the second embodiment. The first version is a simplified version of the sweat collection article 52 shown on the person's arm in FIG. 3. As shown in FIG. 4, the sweat collecting article 52 comprises a thin, flexible, conformable, and impervious covering 54. The term "thin", as used herein, means that the covering 54 has a thickness of less than or equal to about 1 mm. The term "flexible", as used herein, means that the covering 54 will bend under the forces associated with applying the covering 54 to a part of a wearer's body, similar to those forces associated used in applying a bandage or wound dressing to a wound. The term "conformable", as used herein, means that the covering 54 will conform to the configuration of the part of the wearer's body to which it is applied. It may also be desirable for the covering 54 to be at least semi-transparent so that a person conducting the test will be able to see through the covering 54 sufficiently to see when sweat is being collected.

The covering 54 has two surfaces comprising a body-facing surface 58 and an opposing outwardly-oriented surface 60. The covering 54 comprises a central portion 62, edges that define a perimeter 64 of the central portion 62, and a perimeter portion 66 surrounding the central portion 62. The central portion 62 of the body-facing surface 58 is free of adhesive. The perimeter portion 66 has adhesive 68 on the body-facing surface 58 for adhering the covering 56 to a person's skin and for forming a seal around the central portion 62. The adhesive 68 substantially or completely surrounds the central portion 62 to keep the central portion 62 in sufficiently close contact with the wearer's skin so that it does not form a gap or bubble adjacent the wearer's skin and forms a seal to prevent sweat from leaving the area of the wearer's skin covered by the central portion 62, other than through the sweat collector tube 56.

As shown in FIG. 4, the sweat collector tube 56 (which is shown as partially fragmented) has a first end 56A, a second end 56B, and a length that extends between the first and second ends. The first end 56A of the sweat collector tube 56 is positioned adjacent to the covering 54 so that the central portion 62 of the covering overlaps a first portion 70 of the tube. A second portion 72 of the tube 56 extends outward beyond one edge of the central portion 62 of the covering 54 and is adjacent to and is joined to the adhesive 68 on the perimeter portion 66 of the covering. A third portion 74 of the tube 56 extends beyond an edge of the covering 54 to the second end of the tube 56B. The second end 56B of the tube 56 is free to join to an instrument for analyzing the sweat.

Figure 5:
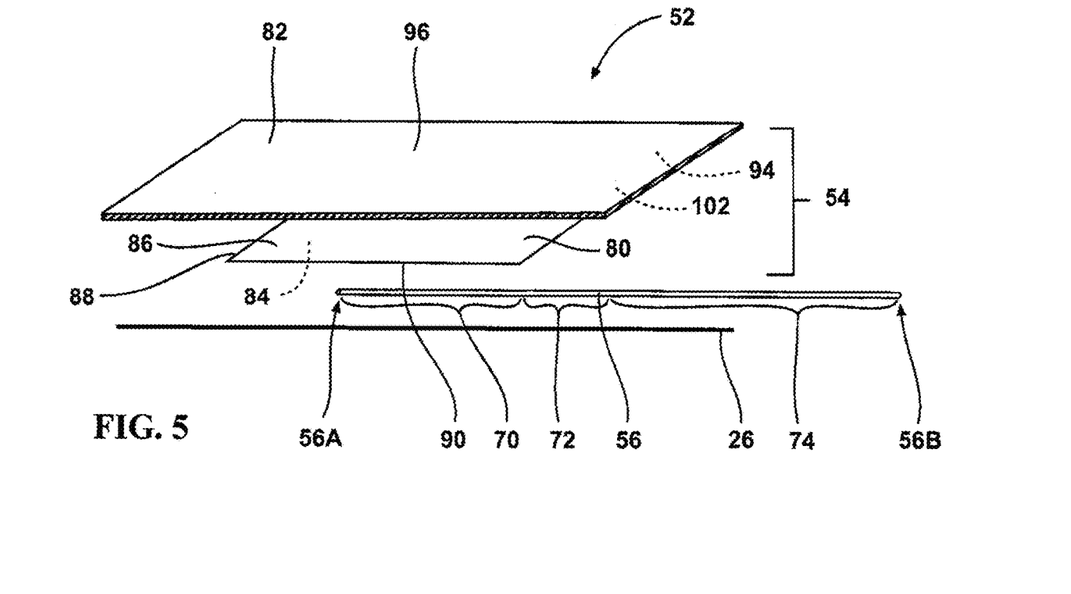
FIG. 5 is an exploded perspective view of another version the sweat collection device shown in FIG. 3.

FIG. 5 shows the assembly of the components of another version of the sweat collecting article 52 of the second embodiment. This is similar to the sweat collecting article 52 shown in FIG. 3. In the sweat collecting article 52 shown in FIG. 5, the covering 54 comprises two pieces comprising a first piece of flexible film material 80 and a second piece of flexible film material 82 with adhesive thereon. The sweat collecting article 52 shown in FIG. 5 is otherwise similar to the sweat collection article 52 shown in FIG. 4. Similar components, such as the tube will, therefore, be given the same numbers. This version of the sweat collecting article may be thought of as a pouch (in the nature of a kangaroo pouch where one part of the pouch is formed by the body of the person wearing the sweat collecting article). It may also be thought of as a laminate.

The first piece of flexible film material 80 has two surfaces comprising a body-facing surface 84 and an opposing outwardly-oriented surface 86, an area, and edges 88 that define a perimeter 90. The first piece of flexible film material 80 fits against the person's skin and entraps sweat between the person's skin and the body-facing surface 84 of the material. The first piece of flexible film 80 should be liquid and vapor impervious, non-porous, non-absorbent, and conformable. The first piece of flexible film 80 may be inextensible. The first piece of flexible film material 80 can comprise any suitable flexible film including polymeric films, such as polyethylene or polypropylene. It may be desirable for the film to comprise virgin, rather than recycled polymeric material, to minimize the presence of contaminants. The first piece of flexible film 80 can be of any size suitable for covering a portion of a person's skin from which sweat will be collected. The size can vary depending on the experiment. In one case, the first piece of flexible film 80 comprises a small piece of plastic film (e.g., between about 2.5-3 inches in length by about 1¼ inch in width).

The second piece of flexible film material 82 has two surfaces comprising a body-facing surface 94 with adhesive thereon and an opposing outwardly-oriented surface 96. The second piece of film material 82 with adhesive thereon is sized and configured to extend beyond all of the edges 88 of the first piece of film material 80. The second piece of flexible film 82 may be liquid impervious, non-absorbent, and conformable, and it may also be moisture vapor permeable and extensible under the forces associated with attaching the second piece of film 82 to a person's skin. The second piece of flexible film material 82 can comprise any suitable flexible film including polymeric films, such as virgin polyethylene or polypropylene. The body-facing surface 94 of the second piece of flexible film material 82 has an adhesive 102 thereon for adhering to the outwardly-oriented surface 86 of the first piece of film material 80 and a person's skin. The adhesive 102 should be suitable for removably attaching the second piece of film 82 to a person's skin. The second piece of film 82 with adhesive thereon can comprise a commercially available bandage material such as OPSITE® transparent waterproof film manufactured by Smith & Nephew, Inc. Advanced Wound Management of Ft. Worth, TX, U.S.A, or TEGADERM™ transparent medical dressing manufactured by 3M™ of St. Paul, MN, U.S.A.

The sweat collector tube 56 in the second embodiment has a first end 56A, a second end 56B, and a body having a length that extends between the first and second ends. The tubing 56 can be the same type and have the same properties as the tubing 36 used above with the first embodiment of the sweat collecting device 32. In the second embodiment, the first end 56A of the sweat collector tube 56 is positioned adjacent to the first piece of film material 80 so that the first piece of film material 80 overlaps a first portion of the tube 70. A second portion 72 of the tube 56 extends outward beyond one edge of the first piece of film 80 and is adjacent to, and is joined to a portion of the adhesive 102 on the second piece of film material 82. The portions of adhesive adjacent to the second portion 72 of the tube 56 may hold the second portion 72 of the tube 56 adjacent to the wearer's skin. A third portion 74 of the tube 56 extends beyond the second piece of film material 82 to the second end 56B of the tube. The second end 56B of the tube is free to join to (and/or to be in fluid communication with) an instrument for analyzing the sweat.

The method of using the second embodiment of the sweat collection system comprises attaching the sweat collection article over an area of the person's skin. The sweat collection article can be attached to any suitable portion of the person's body from which a sweat sample can be obtained. For example, the sweat collection article can be attached to the inside of a person's forearm.

The sweat collection article 52 can be pre-assembled and placed on the person's skin; or it can be assembled as it is placed on the person's skin. In either case, the relationship of the components will be the same. The following will describe assembly of the sweat collection article on the person's skin. The first end 56A of the tubing 56 is placed adjacent the area of the person's skin. Next, a small first piece of plastic film 80 is placed over the first end of the tube 56A so that the first piece of film 80 overlies the first end 56A of the sweat collector tubing 56. There may be a small space between the wearer's skin and the first piece of film 80 to prevent the skin from adhering to first piece of material 80. A second piece of film material 82 with adhesive thereon that is larger than the first piece of film 80 is then obtained. If the second piece of film 82 is in the form of an adhesive bandage, any protective covering on the adhesive is first removed. The second piece of film 82 is applied over the first piece of film 80 so that its edges extend outward from the edges of the small first piece of plastic film 80. The second piece of film material 82 comprises a first portion of adhesive that adheres to the outwardly-oriented surface 86 of the first piece of film material 80 and a second portion of adhesive that adheres to a person's skin. The first and second portions of adhesive on the body-facing surface 94 of the second piece of film 82 may be separated or contiguous. The sweat collector tubing 56 extends outward from under the first and second pieces of film material 80 and 82 to its second end 56B, while the second portion of adhesive adheres part of the tubing 56 to the wearer's skin. The second end 56B of the sweat collector tubing 56 is placed in fluid communication with an instrument for analyzing sweat, and sweat is collected from the person's skin using the sweat collection article wherein sweat travels into the sweat collector tubing 56 and then into the instrument.

The size of the first and second pieces of film 80 and 82 can be adjusted based on the use/type of exercise. The location of the first end 56A of the tubing 56 and the angle that the tubing 56 makes relative to the vertical direction may also be set depending on the type of exercise. For example, if the subject is walking or running on a treadmill, the tube 56 may be oriented downward, since their forearms will be oriented downward. If the subject is on an exercise bike, then their arm will be oriented more horizontally or even with their hand elevated above their elbow. In the latter case, the tubing 56 may be oriented generally horizontally. In either case, it is desirable to position the first end 56A of the tubing 56 at a location under the first piece of film 80 where sweat will most likely flow by gravity.

The second embodiment is utilized by asking participants to perform a sweat collection either through stimulation, heat acclimation, or exercise with the invention worn on a part of their body. It is not necessary to induce sweating through the use of iontophoretic transporting of drug molecules through the skin. The sweat collection article 52 can be placed on the wearer's skin first, and then the person can be instructed to engage in the specified activity. Alternatively, but less desirably, the person may be instructed to initiate the specified exercise, and before the person begins generating sweat, the sweat collection article 52 can be placed on the wearer's skin. As in the case of the first embodiment, it may be desirable for the participant to be positioned close to the instrument to ensure that there is minimal delay between the sweat collection and the analysis. It may, for example, be desirable for the participant to be within about 0.5 meter of the instrument.

The prior art MEGADUCT® device shown in FIG. 1 is generally used to obtain sweat samples which are used to measure for salt content. Other devices or sensors that may have been used for real time analysis of sweat are typically limited to detecting a single predetermined substance, or a limited number of predetermined substances (e.g., less than or equal to five substances) that are known to be present in sweat. The devices and methods of the present invention, on the other hand, are used to discover any substances that may be contained in sweat. The devices and methods of the present invention are also used to determine how the presence or intensity (or abundance) of such substances in sweat may change over the period of collection. The present invention may, for instance, be used to measure for lipids, amino acids, metabolites continuously throughout the collection period. The methods of the present invention can measure for multiple analytes at the same time. For instance, the methods of the present invention can measure for six or more different analytes up to a relatively unlimited number of different analytes (e.g., a thousand or more different analytes). In certain cases, it may be desirable to detect between about 50 and about 500 different analytes at a given time. A scan can be run every second or less (even every millisecond, or every microsecond) on the collected sweat that is transported to the instrument for analyzing sweat. The samples can be analyzed in real time for any substances including, but not limited to the presence of biomarkers as described in U.S. patent application Ser. No. 16/431,326, filed on Jun. 4, 2019 and published as U.S. Patent Application Publication US 2019/0365298 A1, Harshman, et al. The metabolites listed in Table 4 of the Harshman, et al. patent application are of particular interest.

In some embodiments, as shown in FIG. 6, it may be desirable to interpose a step of desalting (or desalinating) the sweat sample prior to analysis by the instrument for analyzing sweat 46. Without wishing to be bound by any particular theory, it is believed that the high salt content of sweat may interfere with the real-time detection of various analytes and biomarkers in sweat due to ion suppression caused by the high salt content. The step of desalting the sweat involves removing salt ions such as $Na^+$, $Cl^-$, $F^-$, $NH_4^+$, $K^+$, and $Ca^{2+}$ from the sweat, without removing other analytes of interest like amino acids and amino acid-like compounds (e.g., molecular weight approximately 50-170 Da). This step removes the salt ions in the sweat (that can be viewed as contaminants) which may improve the instrument's ability to detect other analytes in lower quantities.

Suitable mechanisms for removing salt include, but are not limited to electrodialysis, micro dialysis, and ion concentration polarization. Such microfluidic devices 48 having an input port 48A and an output port 48B can be connected in-line between the sweat collecting device 32 or 52 and the instrument for analyzing sweat 46. Passing the sweat through such devices will not result in an appreciable time delay in the real-time analysis of the collected sweat because the sweat can flow through such devices relatively quickly. For instance, electrodialysis is a membrane separation technology in which the ionized species are allowed to pass through an ion-exchange membrane by means of an external applied electric field. Microdialysis is a minimally-invasive sampling technique that is typically used for continuous measurement of free, unbound analyte concentrations in the extracellular fluid of virtually any tissue. As a result, the device 48 will provide a real-time rate of the migration of sweat from the individual to the instrument for analyzing sweat 46 to facilitate quantitative determination of changes in analyte abundance over time.

Various alternative embodiments of the systems and methods for collecting sweat over a period of time are possible. It is understood that several of the aforementioned steps can be performed in any suitable order. For instance, the method may involve attaching the sweat collection device over a person's skin before or after sweating is induced. In addition, in the second embodiment, the sweat collection article can be assembled first and attached to the wearer's skin; or it can be assembled on the wearer's skin by placing the tube against the wearer's skin and then placing the covering on top of the tube. The free end of the sweat collector tubing may be placed in fluid communication with the input port of an instrument for analyzing sweat either before or after the sweat collection device is placed on a person's skin. In addition, although collection and analysis of sweat from humans is primarily of interest, the system and method of the present invention could be used with any other biological subject that is capable of producing and excreting sweat.

The systems and methods for real-time sweat sampling and analysis described herein can provide a number of advantages including, but not limited to the following. This sweat collecting device and sweat collection and analysis system and method provide for continuous real-time sweat sampling and analysis. The current MACRODUCT® and MEGADUCT® products are primarily used to collect and then later measure the concentration of sodium and chloride in the sweat of children suffering from cystic fibrosis. The systems and methods of the present invention can be used to detect a relatively unlimited number of different analytes in sweat as the sweat is generated and collected, and to monitor any changes in analytes that occur over the period of collection. In the methods of the present invention, sodium and chloride may be removed as contaminants so that the instrument is better able to detect lower quantities of the analytes of interest. Other advantages are listed throughout this description. It should be understood, however, that these advantages need not be required unless they are set forth in the appended claims.

There are numerous, non-limiting embodiments of the invention. All embodiments, even if they are only described as being "embodiments" of the invention, are intended to be non-limiting (that is, there may be other embodiments in addition to these), unless they are expressly described as limiting the scope of the invention. Any of the embodiments described herein can also be combined with any other embodiments in any manner to form still other embodiments.

The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. The term "joined" includes both those configurations in which an element is temporarily joined to another element, or in which an element is permanently joined to another element.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A continuous real-time sweat collection and analysis system comprising:
   a sweat collecting article comprising:
      a thin, flexible, conformable, and impervious covering having two surfaces comprising a body-facing surface and an opposing outwardly-oriented surface, a central portion, edges that define a perimeter of said central portion, and a perimeter portion surrounding said central portion, wherein the perimeter portion has adhesive on the body-facing surface for adhering the covering to a person's skin and for forming a seal around said central portion, and said central portion of the body-facing surface is free of adhesive;
      a sweat collector tube having a first end, a second end, and a length that extends between said first and second ends, wherein the first end of said sweat collector tube is positioned adjacent to said covering so that the central portion of the covering overlaps a first portion of said tube and the adhesive on said perimeter portion of said covering adheres to a second portion of said tube, and a third portion of said tube extends outward beyond an edge of said covering to the second end of said tube, wherein the second end of said tube is free to place in fluid communication with an instrument for analyzing said sweat; and
   an instrument for analyzing sweat collected from a person wherein said instrument has an input port for receiving fluid samples, and the free end of said sweat collector tube is in fluid communication with the input port of said instrument, wherein said instrument is a mass spectrometer and said mass spectrometer is configured to receive sweat samples on a continuous basis from said sweat collection device.

2. The real-time sweat collection system of claim 1 wherein said covering comprises a single piece of film.

3. The real-time sweat collection system of claim 1 wherein said covering comprises two pieces of flexible material comprising:
- a first piece of film material forming said central portion of said covering, said first piece of film material having two surfaces comprising a body-facing surface and an opposing outwardly-oriented surface, an area, and edges that define a perimeter of said first piece of film material; and
- a second piece of film material, wherein said second piece of film material has two surfaces comprising a body-facing surface and an opposing outwardly-oriented surface, wherein said second piece of film material is sized and configured to extend beyond the edges of said first piece of film material, and a first part of the body-facing surface of the second piece of film material has an adhesive thereon for adhering to the outwardly-oriented surface of the first piece of film material, a second part of the body-facing surface of said second piece of film material and the adhesive thereon forms the perimeter portion of said covering for adhering to a person's skin and forming a seal around said central portion of said covering.

4. The sweat collection and analysis system of claim 1 further comprising a device for removing salt from the sweat that is in fluid communication with said sweat collecting device and said instrument and is arranged so that sweat is transported to said device for removing salt from the sweat before it is transported to the instrument for analyzing sweat.

5. The sweat collection and analysis system of claim 4 wherein a device for removing salt from the sweat is selected from the group consisting of: electrodialysis, micro dialysis, and ion concentration polarization devices.

6. A continuous real-time method of collecting and analyzing sweat from a person's skin, said method comprising:
a) attaching a sweat collection article over an area of the person's skin, wherein said sweat collection article comprises:
- a sweat collector tube having a first end and a second end, wherein the first end of said tube is placed adjacent the area of the person's skin, and the second end of sweat collector tube is free to place in fluid communication with an instrument for analyzing sweat; and
- a thin, flexible, conformable, and impervious covering that is positioned over and adhered to the sweat collector tube, said covering having two surfaces comprising a body-facing surface and an opposing outwardly-oriented surface, a central portion, edges that define a perimeter of said central portion, and a perimeter portion surrounding said central portion, wherein said central portion of the body-facing surface is free of adhesive, and the central portion of the cover is placed over the first end of the sweat collector tube, and the perimeter portion has adhesive on the body-facing surface for adhering the covering to a person's skin and for forming a seal around said central portion;
b) placing the free second end of said sweat collector tube in fluid communication with the input port of an instrument for analyzing sweat;
c) collecting sweat from the person's skin using said sweat collection device wherein sweat travels into said sweat collector tubing and then into said instrument; and
d) analyzing the sweat collected using said instrument, wherein said instrument is a mass spectrometer and said mass spectrometer is configured to receive sweat samples on a continuous basis from said sweat collection device.

7. The method of claim 6 wherein said mass spectrometer analyzes the sweat for analytes/ions other than sodium and chloride.

* * * * *